(12) United States Patent
Ida

(10) Patent No.: US 11,141,053 B2
(45) Date of Patent: Oct. 12, 2021

(54) ENDOSCOPE APPARATUS AND CONTROL APPARATUS

(71) Applicant: OLYMPUS CORPORATION, Hachioji (JP)

(72) Inventor: Takayuki Ida, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 449 days.

(21) Appl. No.: 16/117,577

(22) Filed: Aug. 30, 2018

(65) Prior Publication Data

US 2018/0368668 A1 Dec. 27, 2018

Related U.S. Application Data

(63) Continuation of application No. PCT/JP2017/016383, filed on Apr. 25, 2017.

(30) Foreign Application Priority Data

Jun. 6, 2016 (JP) .............................. JP2016-112615

(51) Int. Cl.
*A61B 1/045* (2006.01)
*A61B 1/00* (2006.01)
(Continued)

(52) U.S. Cl.
CPC ............ *A61B 1/045* (2013.01); *A61B 1/0005* (2013.01); *A61B 1/00009* (2013.01);
(Continued)

(58) Field of Classification Search
CPC ... A61B 1/0676; A61B 1/045; A61B 1/00009; A61B 1/0005; A61B 1/00096;
(Continued)

(56) References Cited

U.S. PATENT DOCUMENTS

| 5,196,928 A * | 3/1993 | Karasawa ............ A61B 1/0005 348/239 |
| 2007/0173689 A1* | 7/2007 | Ozaki .................... A61B 1/042 600/111 |

(Continued)

FOREIGN PATENT DOCUMENTS

| JP | 2009-039243 A | 2/2009 |
| JP | 2009-39249 A | 2/2009 |

(Continued)

OTHER PUBLICATIONS

Aug. 1, 2017 International Search Report issued in International Patent Application No. PCT/JP2017/016383.

*Primary Examiner* — Alexandra L Newton
*Assistant Examiner* — Jae Woo
(74) *Attorney, Agent, or Firm* — Oliff PLC

(57) ABSTRACT

An endoscope apparatus includes: a display image selecting portion that selectively outputs one of a surgical image and a gastrointestinal image inputted via an input portion or outputs both of the surgical image and the gastrointestinal image; a combining portion that generates, when both of the surgical image and the gastrointestinal image are outputted by the display image selecting portion, a composite image for performing two-screen display of the surgical image and the gastrointestinal image; and a processor that performs image judgment processing, the processor detecting whether a high-luminance area formed by illumination light radiated at a time of image pickup by the gastrointestinal endoscope exists in the surgical image; and deciding, when detecting that the high-luminance area exists in the surgical image when the surgical image is displayed in one screen, a display method for causing two-screen display based on the composite image to be displayed.

8 Claims, 6 Drawing Sheets

(51) Int. Cl.
  *G02B 23/24* (2006.01)
  *A61B 1/06* (2006.01)
  *A61B 1/273* (2006.01)

(52) U.S. Cl.
  CPC ...... *A61B 1/00096* (2013.01); *A61B 1/00163* (2013.01); *G02B 23/2407* (2013.01); *A61B 1/0676* (2013.01); *A61B 1/2736* (2013.01); *G02B 23/24* (2013.01)

(58) Field of Classification Search
  CPC .............. A61B 1/00163; A61B 1/2736; A61B 2090/371; A61B 2576/00; A61B 2576/02; G02B 23/2407; G02B 23/24; H04N 5/2256
  See application file for complete search history.

(56) References Cited

U.S. PATENT DOCUMENTS

| | | | |
|---|---|---|---|
| 2008/0281189 A1* | 11/2008 | Komuro | A61B 8/445 600/424 |
| 2009/0137868 A1* | 5/2009 | Yamaguchi | A61B 1/042 600/109 |
| 2019/0051039 A1* | 2/2019 | Tsuru | G06T 5/008 |
| 2019/0083180 A1* | 3/2019 | Ichiki | G02B 23/24 |
| 2019/0096037 A1* | 3/2019 | Fukazawa | G06T 5/003 |
| 2020/0008653 A1* | 1/2020 | Kamon | A61B 1/00009 |
| 2020/0098104 A1* | 3/2020 | Kashima | G02B 23/24 |
| 2020/0113423 A1* | 4/2020 | Yamazaki | A61B 1/0676 |
| 2020/0175719 A1* | 6/2020 | Wright | G06T 7/74 |

FOREIGN PATENT DOCUMENTS

| | | |
|---|---|---|
| JP | 2009-112644 A | 5/2009 |
| JP | 2009-125297 A | 6/2009 |

* cited by examiner

ENDOSCOPE APPARATUS AND CONTROL APPARATUS

CROSS REFERENCE TO RELATED APPLICATION

This application is a continuation application of PCT/JP2017/016383 filed on Apr. 25, 2017 and claims benefit of Japanese Application No. 2016-112615 filed in Japan on Jun. 6, 2016, the entire contents of which are incorporated herein by this reference.

BACKGROUND OF INVENTION

1. Field of the Invention

The present invention relates to an endoscope apparatus and a control apparatus that are suitable for a procedure using a surgical endoscope and a gastrointestinal endoscope.

2. Description of the Related Art

Conventionally, laparoscopic surgery (hereinafter also referred to as surgical operation) in which therapeutic treatment is performed without performing laparotomy has been performed for the purpose of reducing invasion into a patient. In the surgical operation, an endoscope for observation (hereinafter referred to as a surgical endoscope) is inserted into a body cavity via a trocar inserted into an abdomen of a patient. In addition to the surgical endoscope inserted into the abdominal cavity via the trocar, for example, an endoscope inserted into a lumen of a large intestine or the like (hereinafter referred to as a gastrointestinal endoscope) may be adopted. For example, at the time of performing an operation of a digestive organ such as a stomach and a duodenum, a gastrointestinal endoscope and a surgical endoscope may be used at the same time. By performing observation from an outside of a lumen by the surgical endoscope and performing observation from an inside of the lumen by the gastrointestinal endoscope, it is possible to perform a procedure with little invasion.

Image pickup signals obtained by performing image pickup by the endoscopes are supplied to camera control units (hereinafter referred to as CCUs) configured to perform image processing. The CCUs perform predetermined image signal processing for the image pickup signals from the endoscopes to obtain endoscopic images. By supplying the endoscopic images from the CCUs to a monitor, the endoscopic images can be seen on a display screen of the monitor. Generally, the image pickup signals from the two endoscopes are supplied to the separate CCUs and signal-processed, respectively.

A surgical endoscopic image (a surgical image) and a gastrointestinal endoscopic image (a gastrointestinal image) from the respective CCUs are supplied to the common monitor so that a doctor can easily confirm at the time of performing a procedure. The monitor can select each of the surgical image and the gastrointestinal image to separately display the images, and can also combine and display the two images in a picture-in-picture (PIP) scheme or a picture-out-picture (POP) scheme.

In Japanese Patent Application Laid-Open Publication No. 2009-39243, an apparatus is disclosed in which an image from a gastrointestinal endoscope is inputted to a CCU configured to perform image processing for a surgical endoscope, and combination of two images is performed in the CCU to output the images to a monitor. In this case, it is possible to switch between one-screen display and two-screen display by operating the CCU.

In a procedure using a surgical endoscope and a gastrointestinal endoscope, while a doctor in charge of a surgical operation is observing a lumen from outside using the surgical endoscope, the gastrointestinal endoscope is inserted from a mouth or the like to a target region by a scopist. Note that the scopist who inserts the gastrointestinal endoscope performs the insertion work while watching display on a monitor dedicated to the scopist. The doctor in charge of the surgical operation causes a surgical image to be displayed on the whole screen of a monitor in consideration of ease of seeing until the gastrointestinal endoscope reaches the target region. Then, when the gastrointestinal endoscope reaches the target region by the scopist, the doctor in charge of the surgical operation gives an instruction to perform two-screen display of the surgical image and a gastrointestinal image. By performing two-screen display, a procedure with little invasion becomes possible.

Note that the doctor in charge of the surgical operation judges that the gastrointestinal endoscope has reached the target region, for example, by illumination light by the gastrointestinal endoscope being observed in the surgical image.

SUMMARY OF THE INVENTION

An endoscope apparatus according to an aspect of the present invention is provided with: an input portion configured to receive a surgical image obtained by a surgical endoscope configured to observe a treatment target organ from outside and a gastrointestinal image obtained by a gastrointestinal endoscope configured to observe the treatment target organ from inside; a display image selecting portion configured to selectively output one of the surgical image and the gastrointestinal image inputted via the input portion or output both of the surgical image and the gastrointestinal image; a combining portion configured to, when both of the surgical image and the gastrointestinal image are outputted by the display image selecting portion, generate a composite image for performing two-screen display of the surgical image and the gastrointestinal image; and a processor configured to perform image judgment processing, the processor being configured to: detect whether a high-luminance area formed by illumination light radiated at a time of image pickup by the gastrointestinal endoscope exists in the surgical image; and decide, when detecting that the high-luminance area exists in the surgical image when the surgical image selected by the display image selecting portion is displayed in one screen, a display method for causing the display image selecting portion to select both of the surgical image and the gastrointestinal image and causing two-screen display based on the composite image to be displayed.

An control apparatus according to an aspect of the present invention is provided with: an input portion configured to receive a surgical image obtained by a surgical endoscope configured to observe a treatment target organ from outside and a gastrointestinal image obtained by a gastrointestinal endoscope configured to observe the treatment target organ from inside; a display image selecting portion configured to selectively output one of the surgical image and the gastrointestinal image inputted via the input portion or output both of the surgical image and the gastrointestinal image; a combining portion configured to, when both of the surgical image and the gastrointestinal image are outputted by the display image selecting portion, generate a composite image for performing two-screen display of the surgical image and the gastrointestinal image; and a processor configured to perform image judgment processing, the processor being configured to: detect whether a high-luminance area formed by illumination light radiated at a time of image pickup by the gastrointestinal endoscope exists in the surgical image; and decide, when detecting that the high-luminance area exists in the surgical image when the surgical image selected by the display image selecting portion is displayed in one screen, a display method for causing the display image selecting portion to select both of the surgical image and the gastrointestinal image and causing two-screen display based on the composite image to be displayed.

BEST MODE FOR CARRYING OUT THE INVENTION

An embodiment of the present invention will be described below in detail with reference to drawings.

Figure 1:
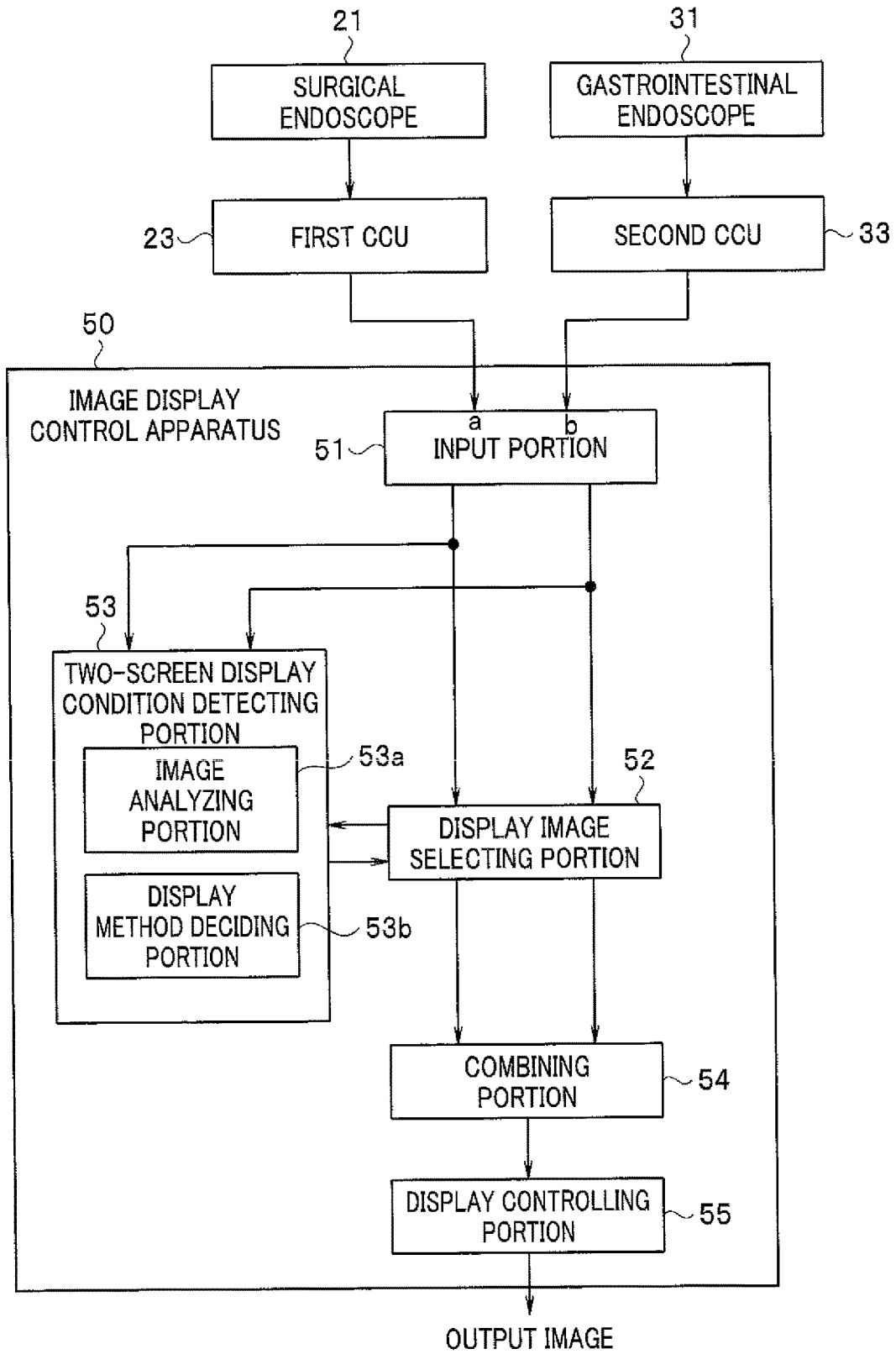
FIG. 1 is a block diagram showing an endoscope apparatus according to an embodiment of the present invention.
Figure 2:
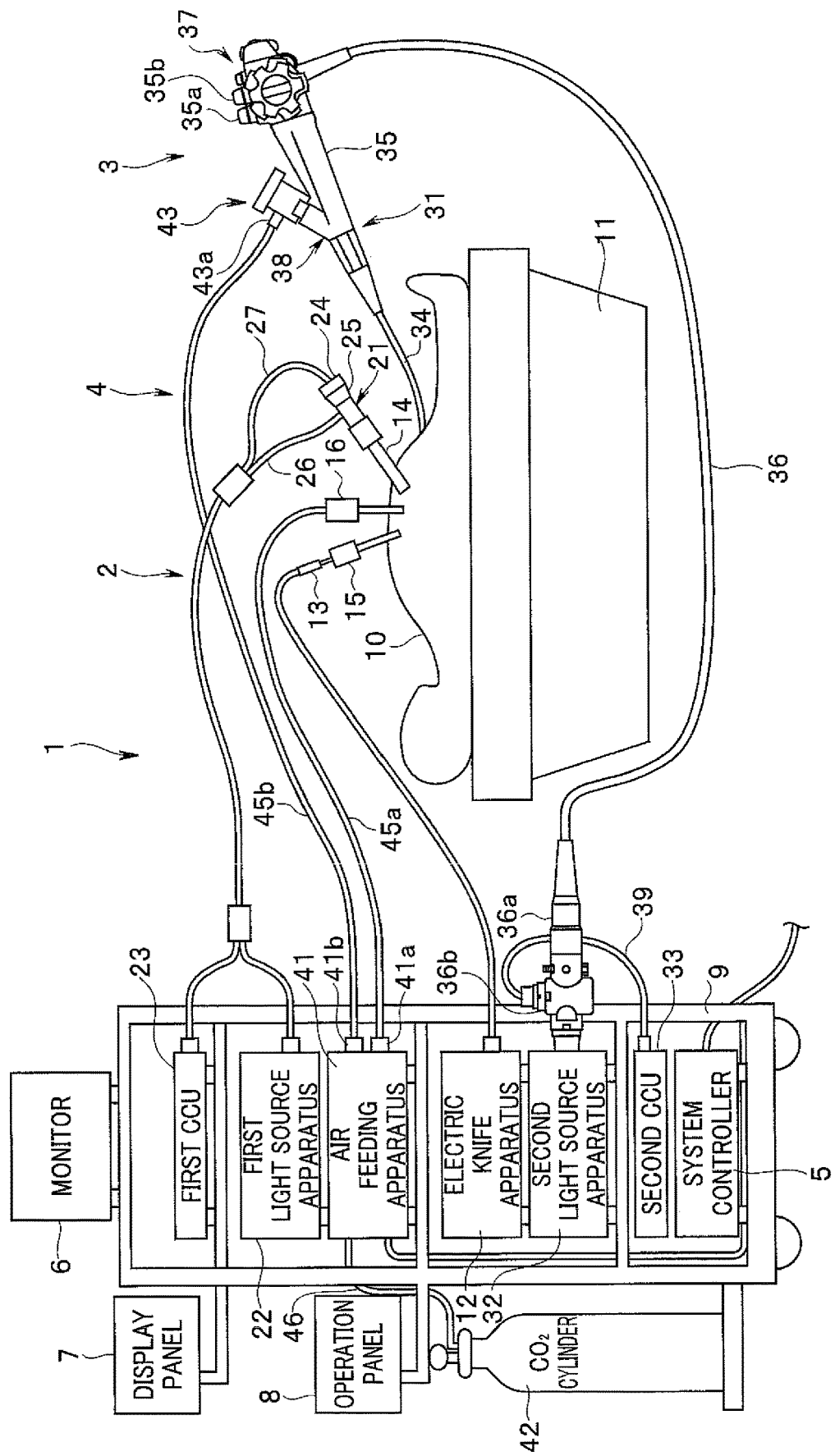
FIG. 2 is an explanatory diagram showing an overall configuration of a medical system that includes the endoscope apparatus of FIG. 1.

FIG. 1 is a block diagram showing an endoscope apparatus according to an embodiment of the present invention. FIG. 2 is an explanatory diagram showing an overall configuration of a medical system that includes the endoscope apparatus of FIG. 1.

The present embodiment makes it possible to, at the time of observation by a surgical endoscope, automatically display a composite image of a surgical image and a gastrointestinal image without requiring an operation by a surgeon or the like by detecting a gastrointestinal endoscope having reached a target region.

First, an overall configuration of a medical system 1 arranged in an operating room will be described using FIG. 2. As shown in FIG. 2, a patient bed 11 on which a patient 10 lies down and various kinds of medical apparatuses mounted on a cart 9 are arranged in the operating room. As shown in FIG. 2, the medical system 1 of the present embodiment is provided with a surgical endoscope system 2 including a surgical endoscope 21 and a gastrointestinal endoscope system 3 including a gastrointestinal endoscope 31.

An insertion portion of the surgical endoscope 21 is configured, for example, with a rigid endoscope or the like and has a camera for endoscope 24 on a proximal end side. The surgical endoscope system 2 is configured with a first light source apparatus 22 and a first camera control unit (hereinafter referred to as a first CCU) 23 placed on the cart 9 in addition to the surgical endoscope 21.

The insertion portion (not shown) of the surgical endoscope 21 is inserted into a first trocar 14 and disposed in an abdominal cavity. In the insertion portion, an observation optical system configured with a relay lens (not shown) configured to transmit an object image and the like and an illumination optical system configured with a light guide (not shown) and the like are provided. On a proximal end portion of the insertion portion, an eyepiece portion 25 configured to observe an optical image transmitted by the observation optical system is provided. The camera for endoscope 24 is detachably disposed on the eyepiece portion 25. Inside the camera for endoscope 24, an image pickup device (not shown) is provided.

The first light source apparatus 22 supplies illumination light to the surgical endoscope 21 via a light guide cable 26. Light reflected from an object is formed on an image forming surface of the image pickup device of the camera for endoscope 24 as an object optical image. The camera for endoscope 24 supplies an image pickup signal based on the object optical image to the first CCU 23 via an image pickup cable 27. The first CCU 23 obtains an endoscopic image (a surgical image) by predetermined video signal processing for the image pickup signal from the camera for endoscope 24 and outputs a video signal of the endoscopic image, for example, to a monitor 6 and a centralized display panel 7. Thereby, the endoscopic image (the surgical image) of the object captured by the surgical endoscope 21 is displayed on a screen of the monitor 6 or the centralized display panel 7.

The gastrointestinal endoscope 31 is configured being provided with a flexible insertion portion 34 to be inserted into a lumen of a large intestine or the like, an operation portion 35 and a universal cord 36. The operation portion 35 is provided with an air/water feeding switch 35a and a suction switch 35b, a bending operation knob 37 configured to cause a bending portion not shown to perform a bending operation, and a treatment instrument insertion opening 38 communicating with a treatment instrument channel not shown. On a proximal end portion of the universal cord 36, an optical source connector 36a is provided.

The gastrointestinal endoscope system 3 is configured with a second light source apparatus 32 and a second camera control unit (hereinafter referred to as a second CCU) 33 placed on the cart 9 in addition to the gastrointestinal endoscope 31. The optical source connector 36a is detachably connected to the second light source apparatus 32. Illumination light is supplied from the second light source apparatus 32 to the gastrointestinal endoscope 31 via the optical source connector 36a. In the gastrointestinal endoscope 31, the illumination light is transmitted through a light guide fiber not shown and emitted from an illumination window provided on a distal end portion of the insertion portion 34, which is not shown.

Light reflected from an object is formed on an image forming surface of an image pickup device provided on the distal end portion of the insertion portion 34 as an object optical image. The image pickup device converts the object optical image to an electrical signal and supplies an image pickup signal from the universal cord 36 to the second CCU 33 via an electrical connector 36b and a cable 39. The second CCU 33 obtains an endoscopic image (a gastrointestinal image) by performing predetermined video signal processing for the image pickup signal from the gastrointestinal endoscope 31 and outputs a video signal of the endoscopic image, for example, to the monitor 6 and the centralized display panel 7. Thereby, the endoscopic image (the gastrointestinal image) of the object captured by the gastrointestinal endoscope 31 is displayed on the screen of the monitor 6 or the centralized display panel 7.

Note that the medical system 1 is also provided with an air feeding system 4. The air feeding system 4 is mainly configured with an air feeding apparatus 41, a gas cylinder 42, which is a supply source and which is a carbon dioxide gas supplying portion, and a system controller 5. Carbon dioxide gas is stored in the gas cylinder 42 in a liquefied state.

The air feeding apparatus 41 is provided with a pipe sleeve for supply to abdominal cavity (hereinafter referred to as a first pipe sleeve) 41a which is a first supply pipe sleeve and a pipe sleeve for supply to lumen (hereinafter referred to as a second pipe sleeve) 41b which is a second supply pipe sleeve. One end portion of a tube for abdominal cavity 45a, which is a first tube, is coupled with the first pipe sleeve 41a, and the other end portion of the tube for abdominal cavity 45a is coupled with a third trocar 16.

One end portion of a tube for lumen 45b, which is a second tube, is coupled with the second pipe sleeve 41b, and the other end portion of the tube for lumen 45b is connected with the gastrointestinal endoscope 31. The other end portion of the tube for lumen 45b is connected to a pipe sleeve 43a of a connector 43 connected to a treatment instrument channel opening portion of the gastrointestinal endoscope 31.

That is, carbon dioxide gas from the air feeding apparatus 41 is supplied into a lumen through the treatment instrument channel of the gastrointestinal endoscope 31, via the tube for lumen 45b and the connector 43. Note that the air feeding apparatus 41 and the gas cylinder 42 are coupled via a high pressure gas tube 46.

An electric knife 13, which is a surgical instrument, is connected to an electric knife apparatus 12. The first trocar 14 is a trocar configured to guide an endoscope into an abdominal cavity. A second trocar 15 is a trocar configured to guide treatment instruments for resecting or treating tissue, such as the electric knife 13, into an abdominal cavity. The third trocar 16 is a trocar for guiding gas for pneumoperitoneum supplied from the air feeding apparatus 41 constituting the air feeding system 4, for example, carbon dioxide gas easy to be absorbed into a living body into an abdominal cavity. Note that carbon dioxide gas may be guided into an abdominal cavity from the first trocar 14 or the second trocar 15.

The system controller 5 performs overall control of the whole medical system 1. The centralized display panel 7, a centralized operation panel 8, the electric knife apparatus 12, which is an endoscope peripheral device, the light source apparatuses 22 and 32, the CCUs 23 and 33, the air feeding apparatus 41 and the like are connected to the system controller 5 via a communication line not shown so that bi-directional communication can be performed.

On the screen of the monitor 6, endoscopic images of an object shot by the surgical endoscope 21 and the gastrointestinal endoscope 31 are displayed in response to video signals outputted from the first CCU 23 and the second CCU 33.

A display screen such as a liquid crystal display is provided on the centralized display panel 7. By the centralized display panel 7 being connected to the system controller 5, operation states of endoscope peripheral devices can be centralizedly displayed together with endoscopic images of an object on the display.

The centralized operation panel 8 is configured with a display portion such as a liquid crystal display and a touch sensor portion integrally provided on a display surface of the display portion. The display portion of the centralized operation panel 8 has a display function of causing an operation switch of each endoscope peripheral device and the like as a setting screen and an operation function of operating the operation switch by a predetermined area on the touch sensor portion being touched.

The centralized operation panel 8 is connected to the system controller 5, and it is possible to, by appropriately operating the touch sensor portion displayed on the display portion, remotely perform various operations, settings and the like on the centralized operation panel 8 similarly to directly operating the operation switch provided on each endoscope peripheral device.

In FIG. 1, the endoscope apparatuses in the present embodiment are provided with an image display control apparatus 50. The image display control apparatus 50 can be arranged at any position in the medical system 1 of FIG. 2. For example, the image display control apparatus 50 may be provided in the monitor 6. An input portion 51 of the image display control apparatus 50 is provided with two input terminals a and b configured to capture video signals. An endoscopic image from the first CCU 23 is supplied to one of the input terminals a and b, and an endoscopic image from the second CCU 33 is supplied to the other. The input portion 51 is adapted to capture the endoscopic images (video signals) inputted from the input terminals a and b and give the endoscopic images to a display image selecting portion 52 and a two-screen display condition detecting portion 53.

The display image selecting portion 52 selects one or both of the endoscopic images inputted via the two input terminals a and b of the input portion 51 and outputs the endoscopic image or endoscopic images to a combining portion 54. The display image selecting portion 52 is adapted to, in the case of selectively outputting only a video signal corresponding to one of the two input terminals a and b of the input portion 51, give a selection signal showing which of video signals inputted to the input terminals a and b has been selected, to the two-screen display condition detecting portion 53. Note that the display image selecting portion 52 can also determine an image to be selected, according to an operation by the surgeon.

If the display image selecting portion 52 has selectively outputted only one of the endoscopic images inputted via the two input terminals a and b of the input portion 51, the combining portion 54 gives the selected endoscopic image (hereinafter referred to as the selected image) to a display controlling portion 55 as it is. The combining portion 54 is adapted to, if the display image selecting portion 52 has outputted both of the two endoscopic images inputted via the two input terminals a and b of the input portion 51, generate a composite image by combining the endoscopic images and give a video signal of the composite image to the display controlling portion 55. The display controlling portion 55 is adapted to control display of the monitor 6 to perform image display based on the video signal from the combining portion 54.

It is not decided which of the input terminals a and b of the input portion 51 each of the first CCU 23 and the second CCU 33 is connected to. It is also conceivable that images based on an endoscope other than the surgical endoscope 21 and the gastrointestinal endoscope 31, for example, an ultrasound endoscope are supplied to the input terminals a and b. In the present embodiment, two-screen display is automatically set when a surgical image is one-screen displayed, and it is necessary to judge whether an image selected for one-screen display is a surgical image or not. The two-screen display condition detecting portion 53 includes an image analyzing portion 53a for the judgment function.

The image analyzing portion 53a is adapted to judge whether a selected image selected by the display image selecting portion 52 or an image that is not selected for display (hereinafter referred to as an unselected image) is an image from the gastrointestinal endoscope 31 or not.

Figure 3:
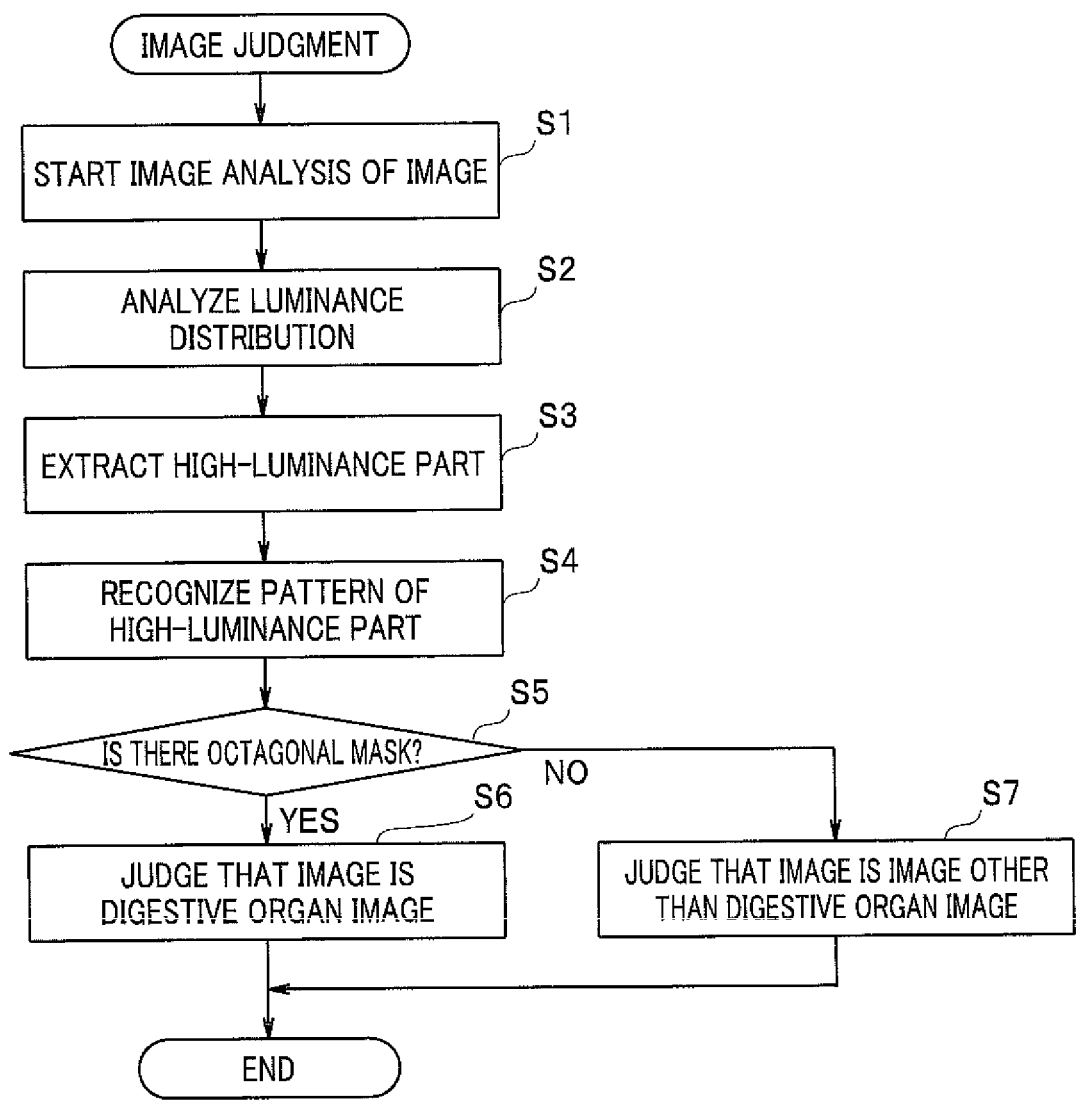
FIG. 3 is a flowchart showing an image judgment flow to judge a gastrointestinal image.

FIG. 3 is a flowchart showing an image judgment flow to judge a gastrointestinal image. In a gastrointestinal image, a part except an octagonal unmasked part is mask-processed, for example, with a black-level mask image. By detecting the mask image by image analysis, the image analyzing portion 53a can judge that an image for which the image analysis has been performed is a gastrointestinal image.

At step S1 in FIG. 3, the image analyzing portion 53a of the two-screen display condition detecting portion 53 starts image analysis of an inputted image. If it is assumed that only two endoscopic images of a surgical image and a gastrointestinal image are inputted to the input portion 51, the image analyzing portion 53a can judge kinds of both images by performing image analysis for one of a selected image and an unselected image.

It is apparent from a selection signal which of video signals inputted to the input terminals a and b of the input portion 51 has been selected to be displayed, and the image analyzing portion 53a performs image analysis for the selected image or the unselected image that are distinguished from the selection signal.

At step S2, the image analyzing portion 53a performs luminance distribution analysis, for example, for the unselected image. Next, at step S3, the image analyzing portion 53a extracts a high-luminance part in the unselected image and performs pattern recognition for the extracted high-luminance part (step S4). The image analyzing portion 53a judges whether the high-luminance part is octagonal or not, that is, whether such a mask image that an unmasked part is octagonal is included or not (step S5). If the mask image is included in the analyzed image, the image analyzing portion 53a judges that the unselected image is a gastrointestinal image (step S6). If the mask image is not included in the analyzed image, the image analyzing portion 53a judges that the unselected image is an image other than a gastrointestinal image (step S7).

In the present embodiment, there is no particular problem in, when it is judged that one of a selected image and an unselected image is a gastrointestinal image, treating the other image as a surgical image. As for an image judged to be an image other than a gastrointestinal image, the image analyzing portion 53a may further judge whether the image other than a gastrointestinal image is an ultrasound image or not by judging whether the image is a black-and-white image or not.

In the present embodiment, by detecting an illumination light image part formed by the gastrointestinal endoscope 31 in a surgical image in a state in which the surgical image is one-screen displayed, a composite image of the surgical image and a gastrointestinal image is caused to be automatically displayed. The two-screen display condition detecting portion 53 is adapted to, if an unselected image is a gastrointestinal image, judge that a selected image is a surgical image and further judge conditions to two-screen display the surgical image and the gastrointestinal image. Note that the two-screen display condition detecting portion 53 may be adapted to, by performing image analysis for a selected image also, judge that the selected image is at least not a gastrointestinal image. Thereby, it is possible to prevent malfunction in a case where both of two inputs are gastrointestinal images.

When illumination light of the gastrointestinal endoscope 31 is radiated into an inside of a lumen, a part irradiated by the illumination light appears as a high-luminance area having a luminance higher than surrounding luminances (hereinafter referred to as an illumination light area) in a surgical image.

If an unselected image is a gastrointestinal image, the image analyzing portion 53a detects whether the illumination light area exists or not by image analysis for a selected image, that is, image analysis for a surgical image. The image analyzing portion 53a analyzes a color of each part of the surgical image. It is thought that image parts of fat, blood, a liver and a surface layer of an abdominal wall other than digestive organs will be image parts with saturations higher than a predetermined saturation. Since illumination light does not exist in the image parts, the areas may be excluded from areas for detecting an illumination light area to detect illumination light. Thereby, detection accuracy can be improved. After that, the image analyzing portion 53a sets areas with saturations lower than the predetermined saturation (hereinafter referred to as low-saturation areas) as detection areas. The low-saturation areas include image parts of a digestive tract mucosa, gauze, forceps and the like with low saturations.

In endoscopic observation, too bright parts because of reflection of illumination light and, on the contrary, parts with an extremely small amount of light occur according to an illumination light radiation state and the like. Therefore, in a surgical image, high-luminance parts such as halation and low-luminance parts with significantly low luminances exist. Such high-luminance parts and low-luminance parts may be also excluded from an illumination light area detection range. Thereby, it is possible to prevent a rough circle existing in halation or a bright spot in a dark part from being misdetected and improve detection accuracy. The image analyzing portion 53a performs luminance distribution analysis for low-saturation areas to detect high-luminance parts and low-luminance parts, and sets areas obtained by excluding the high-luminance parts and the low-luminance parts from the low-saturation areas as illumination light area detection areas.

When the gastrointestinal endoscope exists inside a digestive tract mucosa, illumination light radiated from a distal end portion of the gastrointestinal endoscope 31 is transmitted through the digestive tract mucosa, and a transmission part becomes bright. The transmission part becomes an area with a higher luminance in comparison with the mucosa around the transmission part. For example, the image analyzing portion 53a determines luminance differences about each detection area and performs edge processing. By the edge processing, the image analyzing portion 53a can extract an area having a luminance higher than luminances around the area (a high-luminance area). Note that the image analyzing portion 53a may be adapted to detect, for each detection area, detect an image part with a luminance exceeding a predetermined luminance as a high-luminance area depending on an illumination environment.

Furthermore, the image analyzing portion 53a performs pattern recognition for judging whether a shape of a high-luminance area in the detection area is similar to a shape formed by illumination light. For example, the image analyzing portion 53a records information about a shape estimated as a shape of an illumination light area in a memory not shown beforehand and detects whether the shape of the high-luminance area is similar to the shape of the illumination light area or not by comparing the information read from the memory and information about the shape of the high-luminance area. Note that the shape of the illumination light area is often substantially circle. If the shape of the high-luminance area in the detection area is, for example, a rough circle as a result of the pattern recognition, the image analyzing portion 53a judges that the high-luminance area is an illumination light area formed by illumination light of the gastrointestinal endoscope 31.

Note that the shape estimated as the shape of the illumination light area is not limited to a circle but may be a shape partially having a circular arc or a parabola, taking a case into consideration where illumination light is obliquely radiated relative to a wall surface of a luminal organ.

The two-screen display condition detecting portion 53 includes a display method deciding portion 53b. If detecting an illumination light area in a surgical image, the image analyzing portion 53a gives a detection result indicating that effect to the display method deciding portion 53b. The display method deciding portion 53b is adapted to output a screen display command for deciding whether a display method is to be one-screen display or two-screen display, based on a selection signal from the display image selecting portion 52 and the detection result of the image analyzing portion 53a. That is, the display method deciding portion 53b judges whether a selected image is a surgical image or not according to the selection signal and the detection result of the image analyzing portion 53a. Furthermore, the display method deciding portion 53b is adapted to output a two-screen display command to the display image selecting portion 52 if a selected image is a surgical image, and it is shown by the detection result of the image analyzing portion 53a that an illumination light area formed by the gastrointestinal endoscope 31 exists in the surgical image.

The display image selecting portion 52 is adapted to, when a two-screen display command is inputted while one-screen display is performed, output both of video signals constituting a surgical image and a gastrointestinal image inputted via the input terminals a and b of the input portion 51, respectively, to the combining portion 54.

Figure 4:
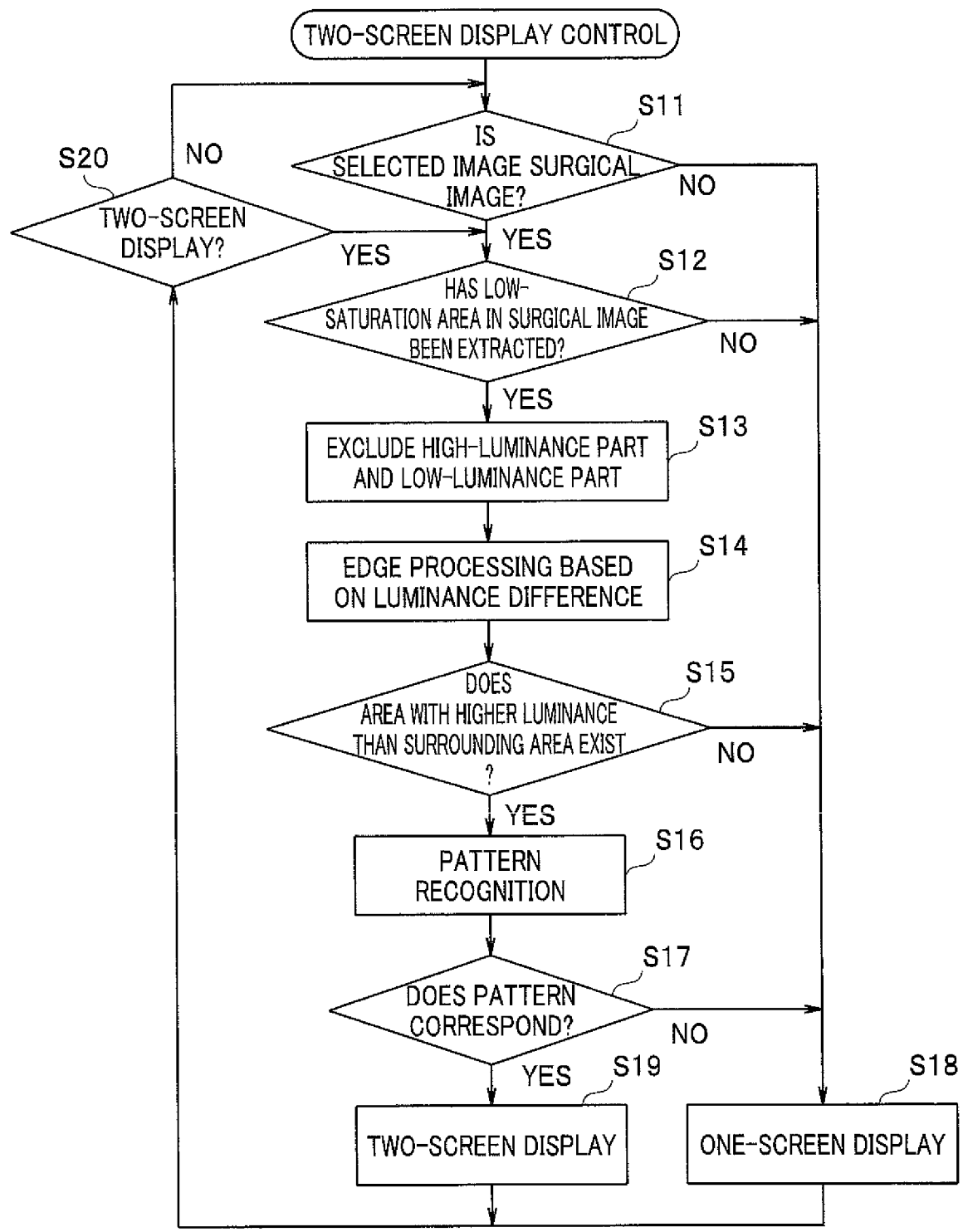
FIG. 4 is a flowchart for illustrating an operation of the embodiment.

Next, an operation of the embodiment configured as described above will be described with reference to FIGS. 4 to 9. FIG. 4 is a flowchart for illustrating the operation of the embodiment. FIGS. 5 to 9 are explanatory diagrams showing examples of display on the display screen of the monitor 6.

Figure 5:
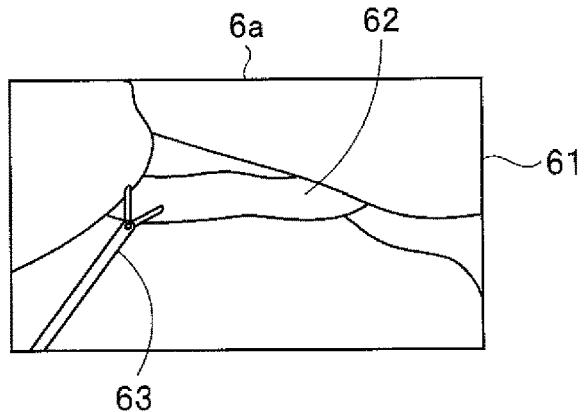
FIG. 5 is an explanatory diagram showing an example of display on a display screen of a monitor 6.

When a surgical image is inputted to only one of the input terminals a and b of the input portion 51, the display image selecting portion 52 outputs the inputted surgical image to the display controlling portion 55 via the combining portion 54 as it is. The surgical image is displayed on the display screen of the monitor 6 by the display controlling portion 55. FIG. 5 shows an example of a surgical image obtained by the surgical endoscope 21. As shown in FIG. 5, a surgical image 61 picked up by the surgical endoscope 21 is displayed on the display screen 6a of the monitor 6. The surgical image 61 is an image of a luminal organ when the luminal organ is seen from outside. In the image, image parts of a luminal organ 62 and forceps 63 are included.

Figure 6:
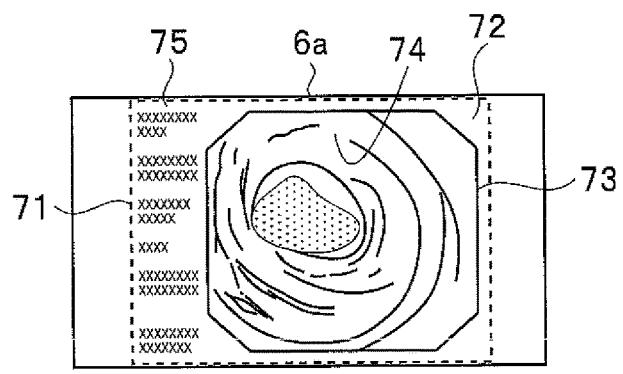
FIG. 6 is an explanatory diagram showing an example of display on the display screen of the monitor 6.

When a gastrointestinal image is inputted to only one of the input terminals a and b of the input portion 51, the display image selecting portion 52 outputs the inputted gastrointestinal image to the display controlling portion 55 via the combining portion 54 as it is. The gastrointestinal image is displayed by the display controlling portion 55. FIG. 6 shows an example of a gastrointestinal image obtained by the gastrointestinal endoscope 31, which is an image of a luminal organ when the luminal organ is seen from inside. As shown in FIG. 6, a gastrointestinal image 71 (a part surrounded by a broken line) outputted from the second CCU 33 is displayed at a center on the display screen 6a of the monitor 6. In the gastrointestinal image 71, an area except for an octagonal unmasked part 73 is masked by a mask image 72 at a substantially black level. On a part of the mask image 72, a display area 75 for displaying patient information and the like is provided.

Next, it is assumed that endoscopic images are inputted to both of the input terminals a and b of the input portion 51. The display image selecting portion 52 can output one or both of the two endoscopic images inputted via the input terminals a and b, for example, based on a user operation. When the display image selecting portion 52 outputs both of the inputted images, the combining portion 54 combines the inputted two endoscopic images to cause a composite image to be displayed by the display controlling portion 55. When the display image selecting portion 52 selects and outputs only one of both of the inputted images, the combining portion 54 causes the selected endoscopic image to be one-screen displayed on the display screen by the display controlling portion 55. In this case, the display image selecting portion 52 outputs a selection signal showing which of video signals inputted to the input terminals a and b has been selected, to the two-screen display condition detecting portion 53.

At step S11 in FIG. 4, the two-screen display condition detecting portion 53 judges whether a selected image is a surgical image or not. For example, if a judgment result showing that an unselected image is a gastrointestinal image is obtained by the image analyzing portion 53a, the two-screen display condition detecting portion 53 judges that the selected image is a surgical image. Note that, even if the unselected image is a gastrointestinal image, it may be further judged whether an image other than a surgical image is displayed as the selected image or not by image analysis for the selected image. If the selected image is a gastrointestinal image, the two-screen display condition detecting portion 53 causes the process to proceed to step S18 and controls the display image selecting portion 52 to maintain one-screen display of the gastrointestinal image.

Now, it is assumed that the display image selecting portion 52 selects only a video signal from the surgical endoscope 21 and supplies the video signal to the combining portion 54, based on a selection operation by the surgeon. In this case, the two-screen display condition detecting portion 53 is given a judgment result that the selected image is a surgical image, and causes the process to proceed to step S12.

At step S12, the two-screen display condition detecting portion 53 extracts low-saturation areas in the selected image. It is thought that saturations of image parts other than the digestive organ are higher than a predetermined saturation. Judging that image parts with saturations higher than the predetermined saturation are parts that need not to be judged, in which a high-luminance area formed by illumination light cannot appear, the two-screen display condition detecting portion 53 extracts the image parts with saturations lower than the predetermined saturation as low-saturation areas. After that, by detecting an illumination light part in the low-saturation areas, detection accuracy can be improved. Note that, if the low-saturation areas cannot be extracted, the two-screen display condition detecting portion 53 proceeds to step S18 and maintains the one-screen display.

Next, at step S13, the two-screen display condition detecting portion 53 excludes high-luminance parts and low-luminance parts from the low-saturation areas to set illumination light detection areas. Next, at step S14, for each detection area, the two-screen display condition detecting portion 53 determines luminance differences and performs edge processing using a predetermined threshold. At step S15, the two-screen display condition detecting portion 53 judges whether or not an area having a luminance higher than surrounding luminances exists as a result of the edge processing of step S14.

If judging that the area having a luminance higher than surrounding luminances does not exist, the two-screen display condition detecting portion 53 causes the process to proceed to step S18 and maintains the one-screen display. If judging that the area having a luminance higher than surrounding luminances exists, the two-screen display condition detecting portion 53 causes the process to proceed to step S16.

The two-screen display condition detecting portion 53 performs pattern recognition for the high-luminance area in the detection area (step S16). At the next step S17, the two-screen display condition detecting portion 53 judges whether or not a result of the pattern recognition corresponds to (or resembles) a shape registered as a shape of an illumination light area. If the pattern corresponds, the two-screen display condition detecting portion 53 judges that the high-luminance area is an illumination light area formed by the gastrointestinal endoscope 31 and causes the process to proceed to step S19. Note that, if the pattern does not correspond, the two-screen display condition detecting portion 53 causes the process to proceed to step S18 and causes the one-screen display to be maintained.

Figure 7:
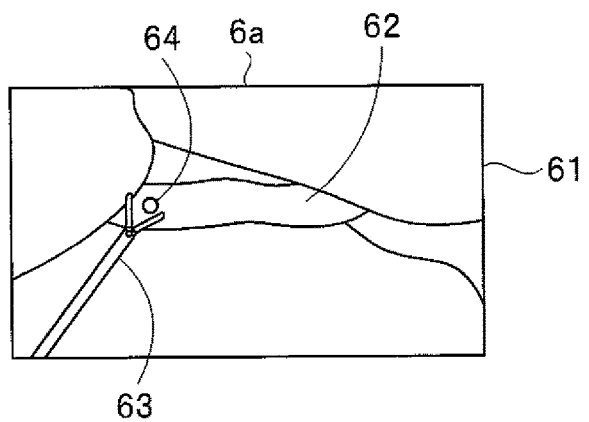
FIG. 7 is an explanatory diagram showing an example of display on the display screen of the monitor 6.

Now, it is assumed that, when the surgical image is one-screen displayed on the display screen 6a of the monitor 6, the distal end portion of the gastrointestinal endoscope 31 inserted into a luminal organ reaches a target region, that is, the luminal organ observed by the surgical endoscope 21. FIG. 7 shows a surgical image displayed on the display screen 6a of the monitor 6 in this case. As shown in FIG. 7, an illumination light area 64 formed by illumination light of the gastrointestinal endoscope 31 appears on the surgical image 61.

When detecting the illumination light area 64 at step S17, the two-screen display condition detecting portion 53 proceeds to step S19, generates a two-screen display command and outputs the two-screen display command to the display image selecting portion 52. When the two-screen display command given, the display image selecting portion 52 outputs both of video signals inputted via the input terminals a and b of the input portion 51 to the combining portion 54. The combining portion 54 combines the two inputs. For example, the combining portion 54 combines the two inputs in a PIP scheme of displaying one of two endoscopic images on a parent screen and displaying the other on a child screen, and outputs a composite image to the display controlling portion 55.

Figure 8:
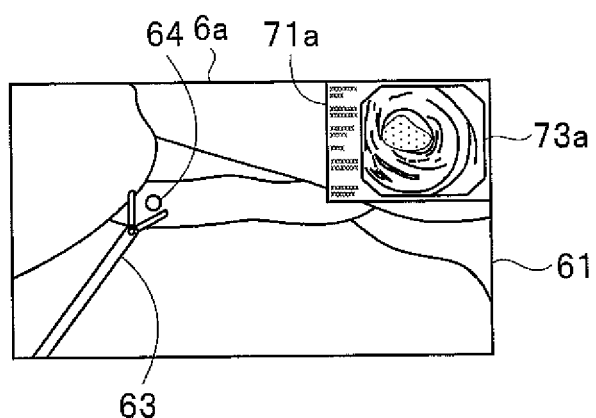
FIG. 8 is an explanatory diagram showing an example of display on the display screen of the monitor 6.

FIG. 8 shows an example of image display in this case. As shown in FIG. 8, the surgical image 61 is parent-screen displayed on the whole display screen 6a of the monitor 6, and a gastrointestinal image 71a is child-screen displayed in a partial area at an upper right of the display screen 6a. An image of an unmasked part 73a in the gastrointestinal image 71a is an image being picked up by the gastrointestinal endoscope 31. A high-luminance part formed by illumination light of the gastrointestinal endoscope 31 is image-displayed in the surgical image 61 as the illumination light area 64. Further, for example, the combining portion 54 may combine the two endoscopic images in a POP scheme of two-screen displaying two endoscopic images arranged side by side, and output a composite image to the display controlling portion 55.

Figure 9:
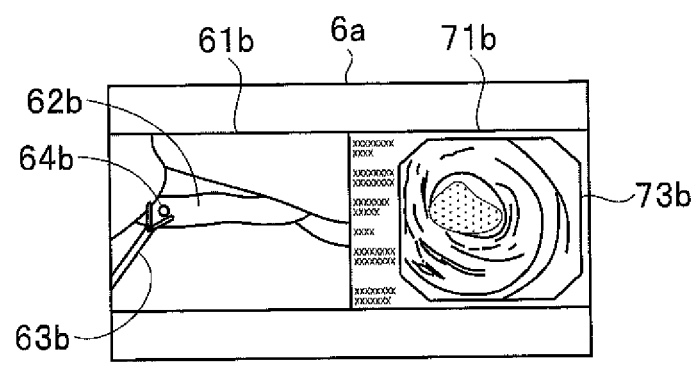
FIG. 9 is an explanatory diagram showing an example of display on the display screen of the monitor 6.

FIG. 9 shows an example of image display in this case. As shown in FIG. 9, a surgical image 61b is displayed in an area on a left side of the display screen 6a of the monitor 6, and a gastrointestinal image 71b is displayed in an area on a right side of the display screen 6a. The surgical image 61b includes image parts of a luminal organ 62b, forceps 63b and an illumination light area 64b being picked up by the surgical endoscope 21. An image of an unmasked part 73b in the gastrointestinal image 71b is an image being picked up by the gastrointestinal endoscope 31. A high-luminance part formed by illumination light of the gastrointestinal endoscope 31 is image-displayed in the surgical image 61b as the illumination light area 64b.

Note that, when the processing of step S18 or S19 ends, the two-screen display condition detecting portion 53 causes the process to proceed to step S20 and judges whether two-screen display is being performed or not. In the case of one-screen display, the process is returned to S11 and repeated. In the case of two-screen display, the process is returned to step S12 and repeated. When the gastrointestinal endoscope 31 is caused to move from the target region luminal organ, the high-luminance part formed by illumination light disappears from the surgical image, and the two-screen display condition detecting portion 53 returns the display to one-screen display at step S18. Note that, in this case, the display may be returned to one-screen display of the endoscopic image selected by a user setting.

As described above, in the present embodiment, at the time of observation by a surgical endoscope, a composite image of a surgical image and a gastrointestinal image is automatically displayed without requiring an operation by a surgeon or the like, by detecting a high-luminance area formed by illumination light of a gastrointestinal endoscope in the surgical image and, thereby, detecting the gastrointestinal endoscope having reached a target region. Thereby, it is possible to certainly detect that the gastrointestinal endoscope has reached a target region, and switch to two-screen display in a short time without the surgeon performing a complicated operation. Thus, smooth progress of a procedure can be promoted.

Note that, as the gastrointestinal endoscope 31, an endoscope capable of both of a normal (white light) observation mode for performing illumination by white light and a narrow band observation mode for performing illumination by narrow band light may be adopted. During white light observation as well as during narrow band observation, an illumination light area has a higher luminance in comparison with a surrounding area. Therefore, during the white light observation as well as during the narrow band observation, detection of an illumination light area is possible. Note that, by setting the threshold for the edge processing at step S14 in FIG. 4 suitable for the narrow band observation, it becomes possible to detect an illumination light area without changing the setting even at the time of white light observation.

The present invention is not limited to the above embodiment as it is, but the components can be modified and embodied within a range not departing from the spirit of the invention at an implementation stage. Further, various inventions can be formed by appropriately combining a plurality of components disclosed in the above embodiment.

For example, some components among all the components shown in the embodiment may be deleted.

What is claimed is:

1. An endoscope apparatus comprising:
an image display controller configured to:
   receive via input terminals a surgical image obtained by a surgical endoscope configured to observe a treatment target organ from outside a lumen of the treatment target organ and a gastrointestinal image obtained by a gastrointestinal endoscope configured to observe the treatment target organ from inside the lumen of the treatment target organ;
   select one of the surgical image and the gastrointestinal image received by the image display controller or select both of the surgical image and the gastrointestinal image for output based on a user operation;
   when both of the surgical image and the gastrointestinal image are selected for output, generate a composite image for performing two-screen display of the surgical image and the gastrointestinal image; and
   perform image judgment processing including:
      detecting whether a high-luminance area formed by illumination light radiated at a time of image pickup by the gastrointestinal endoscope exists in the surgical image; and
      when detecting that the high-luminance area exists in the surgical image in a state in which the surgical image is displayed in one screen, selecting both of the surgical image and the gastrointestinal image for output and causing a two-screen display based on the composite image to be displayed.

2. The endoscope apparatus according to claim 1, wherein the image display controller is configured to detect luminance distribution of the surgical image and detect an area with a luminance exceeding a predetermined threshold as the high-luminance area.

3. The endoscope apparatus according to claim 1, wherein the image display controller is configured to detect luminance distribution of the surgical image and detect an area with a luminance higher than surrounding luminances as the high-luminance area.

4. The endoscope apparatus according to claim 3, wherein the image display controller is configured to detect the area having the luminance higher than the surrounding luminances by determining luminance differences of the surgical image and performing edge processing.

5. The endoscope apparatus according to claim 1, wherein the image display controller is configured to:
   perform color analysis of the surgical image to extract a low-saturation area having a saturation lower than a predetermined saturation, and
   detect the high-luminance area in the low-saturation area.

6. The endoscope apparatus according to claim 5, wherein the image display controller is configured to set a part having a luminance within a predetermined luminance range, in the low-saturation area as a detection range for detecting the high-luminance area.

7. The endoscope apparatus according to claim 1, wherein the image display controller is configured to judge whether the high-luminance area is an area formed by the illumination light radiated at the time of image pickup by the gastrointestinal endoscope or not by pattern recognition between a shape of the high-luminance area and a predetermined shape.

8. A control apparatus comprising:
an image display controller configured to:
   receive via input terminals a surgical image obtained by a surgical endoscope configured to observe a treatment target organ from outside a lumen of the treatment target organ and a gastrointestinal image obtained by a gastrointestinal endoscope configured to observe the treatment target organ from inside the lumen of the treatment target organ;
   select one of the surgical image and the gastrointestinal image received by the image display controller or select both of the surgical image and the gastrointestinal image for output based on a user operation;
   when both of the surgical image and the gastrointestinal image are selected for output, generate a composite image for performing two-screen display of the surgical image and the gastrointestinal image; and
   perform image judgment processing including:
      detecting whether a high-luminance area formed by illumination light radiated at a time of image pickup by the gastrointestinal endoscope exists in the surgical image; and
      when detecting that the high-luminance area exists in the surgical image in a state in which the surgical image is displayed in one screen, selecting both of the surgical image and the gastrointestinal image for output and causing a two-screen display based on the composite image to be displayed.

* * * * *